US012565480B2

(12) United States Patent
Zhang et al.

(10) Patent No.: US 12,565,480 B2
(45) Date of Patent: Mar. 3, 2026

(54) THIOPHENE DERIVATIVES AS XANTHINE OXIDASE INHIBITORS AND APPLICATION THEREOF

(71) Applicant: Tonghua Dongbao Pharmaceutical Co., Ltd., Tonghua County (CN)

(72) Inventors: Yang Zhang, Shanghai (CN); Wentao Wu, Shanghai (CN); Wenyuan Zhu, Shanghai (CN); Shuhui Chen, Shanghai (CN)

(73) Assignee: Tonghua Dongbao Pharmaceutical Co., Ltd., Tonghua County (CN)

( * ) Notice: Subject to any disclaimer, the term of this patent is extended or adjusted under 35 U.S.C. 154(b) by 853 days.

(21) Appl. No.: 17/766,435

(22) PCT Filed: Oct. 30, 2020

(86) PCT No.: PCT/CN2020/125191

§ 371 (c)(1),
(2) Date: Apr. 4, 2022

(87) PCT Pub. No.: WO2021/083319

PCT Pub. Date: May 6, 2021

(65) Prior Publication Data

US 2023/0322703 A1 Oct. 12, 2023

(30) Foreign Application Priority Data

Oct. 30, 2019 (CN) ......................... 201911049951.7
Feb. 21, 2020 (CN) ......................... 202010110482.1

(51) Int. Cl.
*C07D 333/70* (2006.01)
*A61P 19/06* (2006.01)
*C07D 495/04* (2006.01)

(52) U.S. Cl.
CPC ............ *C07D 333/70* (2013.01); *A61P 19/06* (2018.01); *C07D 495/04* (2013.01)

(58) Field of Classification Search
CPC .................................................... C07D 333/70
See application file for complete search history.

(56) References Cited

U.S. PATENT DOCUMENTS 10,266,496 B2 * 4/2019 Yang ....................... A61P 13/02

FOREIGN PATENT DOCUMENTS

CN 106478500 A 3/2017
JP 2018-532698 A 11/2018
JP 2019-519606 A 7/2019
WO WO 2006023462 * 3/2006
WO WO-2006023462 A1 * 3/2006 ......... C07D 207/327
WO WO 2008/126899 A1 10/2008
WO WO 2010/044403 A1 4/2010

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
Dorwald F. A. Side Reactions in Organic Synthesis, 2005, Wiley: VCH, Weinheim p. IX of Preface p. 1-15.*
Venkatesh, J. Pharm. Sci. 89, 145-154 (2000) (p. 146, left column).*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Dua et al., Acute kidney injury observed during phase 1 clinical trials of a novel xanthine oxidase/URAT1 dual inhibitor PF-06743649. Clin Rheumatol. Aug. 2016;35(8):2045-2051. Epub Apr. 19, 2016.
Nozaki et al., Structure Activity Correlation and Drug Design. Chemistry for Drug Dev. Jul. 1, 1995. 7 pages.

* cited by examiner

*Primary Examiner* — Nizal S Chandrakumar
(74) *Attorney, Agent, or Firm* — Mintz Levin Cohn Ferris Glovsky and Popeo, P.C.

(57) ABSTRACT

A class of xanthine oxidase (XO) inhibitors, and application thereof in the preparation of drugs for treating XO-related diseases. Specifically disclosed is a compound represented by formula (I) and a pharmaceutically acceptable salt thereof.

(I)

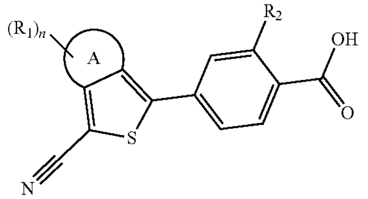

6 Claims, No Drawings

THIOPHENE DERIVATIVES AS XANTHINE OXIDASE INHIBITORS AND APPLICATION THEREOF

CROSS REFERENCE TO RELATED APPLICATIONS

The present application is a national application of PCT/CN2020/125191, filed on Oct. 30, 2020, which claims the priority of the Chinese Patent Application No. 201911049951.7, filed on Oct. 30, 2019, and the Chinese Patent Application No. 202010110482.1, filed on Feb. 21, 2020. The entire contents of the Chinese Patent Applications Nos. 201911049951.7 and 202010110482.1 are incorporated by reference herein as part of the disclosure of the present application.

The present disclosure claims the priority of:
CN201911049951.7, filed on Oct. 30, 2019; and
CN202010110482.1, filed on Feb. 21, 2020.

FIELD OF THE INVENTION

The present disclosure relates to xanthine oxidase (XO) inhibitors, and application thereof in the preparation of drugs for treating XO-related diseases. Specifically disclosed is a compound represented by formula (I) and a pharmaceutically acceptable salt thereof.

BACKGROUND OF THE INVENTION

Gouty arthritis is a common and complex type of arthritis. When the concentration of uric acid in the human blood exceeds 7 mg/dL, uric acid deposits in the joints, cartilage and kidneys as a monosodium salt, causing excessive (sensitized) body's immune system and thus bringing about painful inflammation. The common attack sites are joint of the big toe, ankle joint, knee joint, etc. Hyperuricemia is the pathological basis of gouty arthritis. Hyperuricemia refers to a condition in which the metabolism of purine substances in the human body is disordered, resulting in an increased synthesis or a decreased excretion of uric acid in the human body, and an abnormally high level of uric acid in the blood. Internationally, the diagnosis of HUA is defined as: under a normal purine diet, fasting serum uric acid levels on two different days: >400 μmol/L (6.8 mg/dL) for men and >360 μmol/L (6 mg/dL) for women. It can be classified into three types: underexcretion, overproduction, and mixed types. Clinical research results have shown that 90% of primary hyperuricemia belong to underexcretion type.

Hyperuricemia is inseparable from gout, and is an independent risk factor for metabolic diseases [diabetes, metabolic syndrome (MS), hyperlipidemia, etc.], chronic kidney disease, cardiovascular disease, and stroke. Therefore, reducing the level of uric acid in the human body can be useful not only for treating or preventing hyperuricemia and gout, but also for reducing the risk of other complications associated with hyperuricemia.

There are two sources of purine in the human body: endogenous purine from self-synthesis or nucleic acid degradation (about 600 mg/d), and exogenous purine from ingested purine diet (about 100 mg/d). Under normal conditions, the uric acid pool in the body is 1200 mg, and the daily production of uric acid is about 700 mg, of which ⅔ is excreted by the kidneys, ⅓ is excreted from the intestine, and a very small amount is excreted through the sweat glands. Therefore, uric acid-lowering drugs currently commonly used in clinical practice include Xanthine Oxidase inhibitors (such as: allopurinol and febusteine, etc.) that inhibit the production of uric acid and Urat1 inhibitors (benbromarone and Resinard, etc.) that are uricosuric.

Xanthine oxidase is an enzyme with low specificity, which can not only catalyze hypoxanthine to form xanthine, and then generate uric acid, but also directly catalyze xanthine to form uric acid. Xanthine oxidase inhibitors are the first-line drugs for the treatment of hyperuricemia. Currently, the main drugs on the market are allopurinol and febusteine. However, such drugs cannot meet the clinical needs of all patients and have significant side effects. Allopurinol is the only uric acid lowering therapy available worldwide, but it has been associated with serious cutaneous adverse events. Allopurinol-related severe hypersensitivity reactions are closely related to leukocyte antigen (HLA)-B*5801, and Chinese people have an HLA-B*5801 positive rate (6%-8%) higher than that of white people (~2%) and have greater risk of the occurrence of hypersensitivity reaction. The uric acid lowering effect of febusteine is better than that of allopurinol, but at a high dose of 80 mg/day, 40% to 52% of patients do not achieve the expected goal of lowing uric acid, and attacks of acute gout are increased. In November 2017, the U.S. Food and Drug Administration issued a statement that febuxostat may actually increase heart-related and all-cause deaths compared with allopurinol and further study is needed.

PF-06743649 is the only dual-target inhibitor of xanthine oxidase and Urat1 that has entered clinical research stage. However, in the clinical phase I trial, 2 subjects developed acute PF-06743649-induced renal injury side effects after administration. The analysis suggested that this may be related to the precipitation of uric acid in the renal tubules caused by the higher Urat1 inhibitory activity of PF-06743649 (Clin Rheumatol. 2016, 35, 2045-2051).

According to the above analysis, there is still an unmet clinical need for safe and effective uric acid-lowering drugs in the market.

The xanthine oxidase inhibitor of the present disclosure has good xanthine oxidase inhibitory activity, and is expected to have a good effect of lowering uric acid in the blood of the human body.

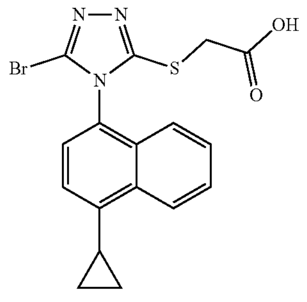

Lesinurad

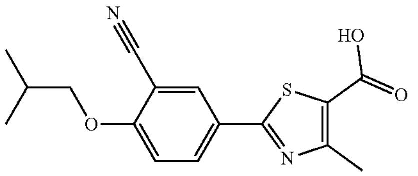

Febuxostat

-continued

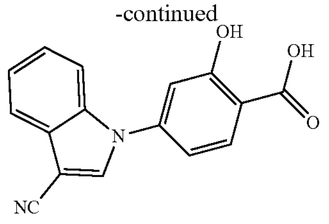

PF-06743649

SUMMARY OF THE INVENTION

The present disclosure provides a compound represented by formula (I) or a pharmaceutically acceptable salt thereof, (I)

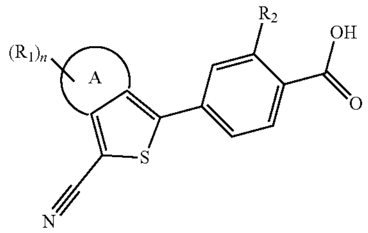

wherein, each $R_1$ is independently selected from H, halogen, OH, $NH_2$, CN, $C_{1-3}$ alkyl, and $C_{1-3}$ alkoxy, and the $C_{1-3}$ alkyl and the $C_{1-3}$ alkoxy are optionally substituted with 1, 2 or 3 $R_a$;

n is selected from 0, 1, 2, 3, and 4;

$R_a$ is selected from H, F, Cl, Br, I, OH, and $NH_2$;

$R_2$ is selected from H, halogen, OH, $NH_2$, and CN; and ring A is selected from $C_{5-6}$ cycloalkyl and 5-6 membered heterocycloalkyl.

In some aspects of the present disclosure, each of the above $R_1$ is independently selected from H, F, Cl, Br, I, OH, $NH_2$, $CH_3$, $CH_3CH_2$, and $CH_3O$, and the $CH_3$, the $CH_3CH_2$, and the $CH_3O$ are optionally substituted with 1, 2 or 3 $R_a$, and other variables are as defined in the present disclosure.

In some embodiments of the present disclosure, each of the above $R_1$ is independently selected from H, F, Cl, Br, I, OH, $NH_2$, $CH_3$, $CH_3CH_2$, $CH_3O$, and $CF_3$, and other variables are as defined in the present disclosure.

In some embodiments of the present disclosure, the above ring A is selected from cyclopentyl, cyclohexyl, tetrahydrofuranyl, pyrrolidinyl, tetrahydropyranyl, dioxanyl and piperidyl, and other variables are as defined in the present disclosure.

In some embodiments of the present disclosure, the above ring A is selected from cyclopentyl, cyclohexyl, tetrahydrofuranyl and dioxanyl, and other variables are as defined in the present disclosure.

In some embodiments of the present disclosure, the above structural unit

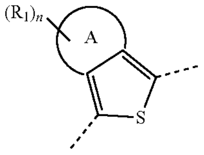 is selected from

-continued

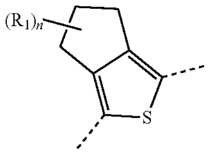,

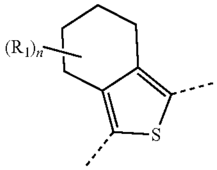,

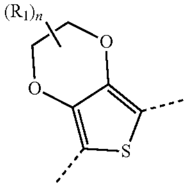, and

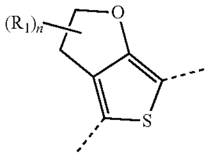, and other variables are as defined in the present disclosure.

In some embodiments of the present disclosure, the above structural unit

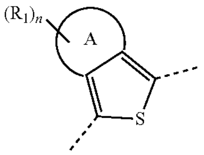 is selected from

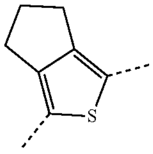,

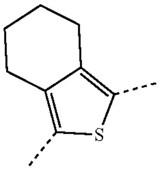,

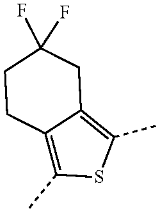,

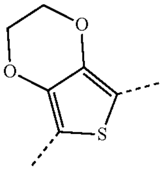,

-continued

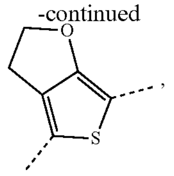

and and other variables are as defined in the present disclosure.

In some embodiments of the present disclosure, the above ring A is selected from cyclopentyl, cyclohexyl, tetrahydrofuranyl, pyrrolidinyl, tetrahydropyranyl, and piperidyl, and other variables are as defined in the present disclosure.

In some embodiments of the present disclosure, the above ring A is selected from cyclopentyl and cyclohexyl, and other variables are as defined in the present disclosure.

Some embodiments of the present disclosure provide the above compound represented by formula (I) or a pharmaceutically acceptable salt thereof,

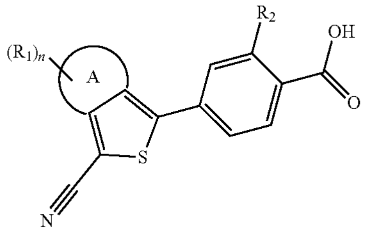

(I)

wherein, each $R_1$ is independently selected from H, halogen, OH, $NH_2$, CN, $C_{1-3}$ alkyl, and $C_{1-3}$ alkoxy, and the $C_{1-3}$ alkyl and the $C_{1-3}$ alkoxy are optionally substituted with 1, 2 or 3 $R_a$;

n is selected from 0, 1, 2, 3, and 4;

$R_a$ is selected from H, F, Cl, Br, I, OH, and $NH_2$;

$R_2$ is independently selected from H, halogen, OH, $NH_2$, and CN; and ring A is selected from $C_{5-6}$ cycloalkyl and 5-6 membered heterocycloalkyl.

In some embodiments of the present disclosure, the above $R_1$ is selected from H, F, Cl, Br, I, OH, $NH_2$, $CH_3$, $CH_3CH_2$, and $CH_3O$, and the $CH_3$, the $CH_3CH_2$, and the $CH_3O$ are optionally substituted with 1, 2 or 3 $R_a$, and other variables are as defined in the present disclosure.

In some embodiments of the present disclosure, the above $R_1$ is selected from H, F, Cl, Br, I, OH, $NH_2$, $CH_3$, $CH_3CH_2$, $CH_3O$, and $CF_3$, and other variables are as defined in the present disclosure.

In some embodiments of the present disclosure, the above ring A is selected from cyclopentyl, cyclohexyl, tetrahydrofuranyl, pyrrolidinyl, tetrahydropyranyl, and piperidyl, and other variables are as defined in the present disclosure.

In some embodiments of the present disclosure, the above ring A is selected from cyclopentyl and cyclohexyl, and other variables are as defined in the present disclosure.

In some embodiments of the present disclosure, the above structural unit

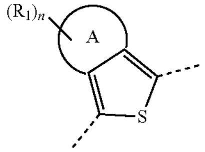

is selected from

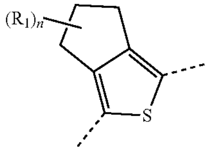

and

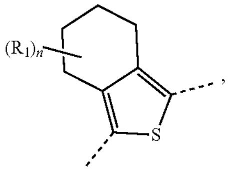

, and other variables are as defined in the present disclosure.

In some embodiments of the present disclosure, the above structural unit

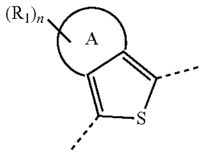

is selected from

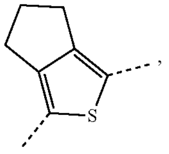

,

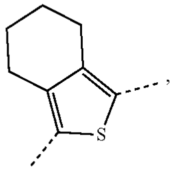

, and

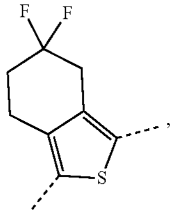

, and other variables are as defined in the present disclosure.

There are also some embodiments of the present disclosure that are formed by any combination of the above variables.

In some embodiments of the present disclosure, the above compound, which is selected from (I-1-1)

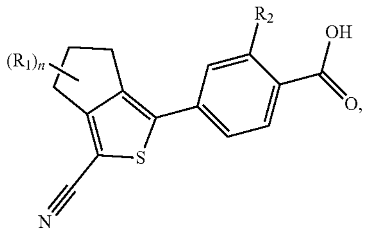

(I-2-1)

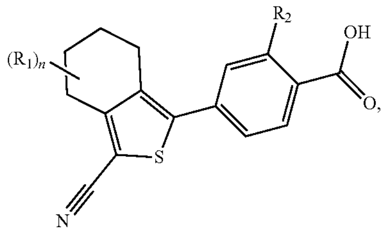

(I-1)

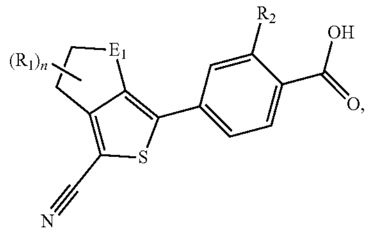

(I-2)

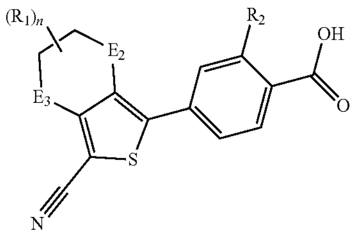

or a pharmaceutically acceptable salt thereof, wherein, $R_1$, n, and $R_2$ as defined in the present disclosure; and $E_1$, $E_2$, and $E_3$ are each independently selected from $CH_2$ and O.

The present disclosure also provides compounds represented by the following formula or a pharmaceutically acceptable salt thereof:

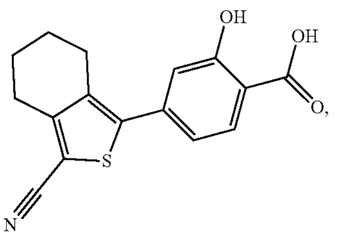

-continued

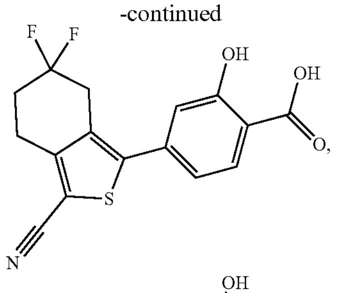

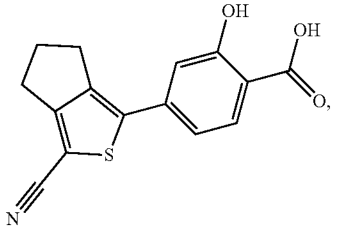

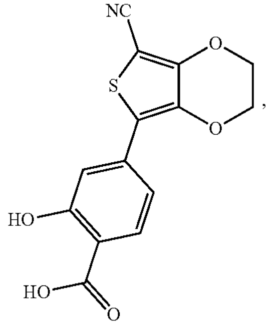

, or

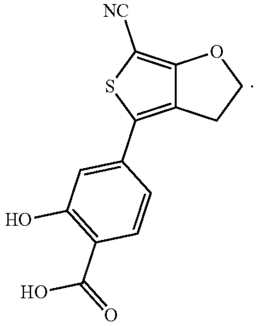

.

In some aspects of the present disclosure, the above compound or a pharmaceutically acceptable salt thereof is useful in the manufacture of a medicament related to a xanthine oxidase inhibitor.

In some aspects of the present disclosure, the above medicament related to a xanthine oxidase inhibitor is useful for treating gouty arthritis and hyperuricemia.

Technical Effect

As a xanthine oxidase inhibitor, the compounds of the present disclosure have good xanthine oxidase inhibitory activity. The related drugs are useful as drug inhibitors for gouty arthritis and hyperuricemia, and have great application prospects in the treatment of gouty arthritis and hyperuricemia.

Definitions and Terms

Unless otherwise specified, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound disclosed herein that is prepared by reacting the compound having a specific substituent disclosed herein with a relatively non-toxic acid or base. When the compound disclosed herein contains a relatively acidic functional group, a base addition salt can be obtained by bringing the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound disclosed herein contains a relatively basic functional group, an acid addition salt can be obtained by bringing the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds disclosed herein contain both basic and acidic functional groups and can be converted to any base or acid addition salt.

The pharmaceutically acceptable salt disclosed herein can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof.

The compound disclosed herein may be present in a specific geometric or stereoisomeric form. The present disclosure contemplates all such compounds, including cis and trans isomer, (−)- and (+)-enantiomer, (R)- and (S)-enantiomer, diastereomer, (D)-isomer, (L)-isomer, and racemic mixture and other mixtures, for example, an enantiomer or diastereomer enriched mixture, all of which are encompassed within the scope disclosed herein. The substituent such as alkyl may have an additional asymmetric carbon atom. All these isomers and mixtures thereof are encompassed within the scope disclosed herein.

Unless otherwise specified, the term "enantiomer" or "optical isomer" refers to stereoisomers that are in a mirrored relationship with each other.

Unless otherwise specified, the term "cis-trans isomer" or "geometric isomer" is produced by the inability of a double bond or a single bond between ring-forming carbon atoms to rotate freely.

Unless otherwise specified, the term "diastereomer" refers to a stereoisomer which has two or more chiral centers in a molecule and is in a non-mirrored relationship between molecules.

Unless otherwise specified, "(+)" means dextroisomer, "(−)" means levoisomer, and "(+)" means racemate.

Unless otherwise specified, a wedged solid bond () and a wedged dashed bond  indicate the absolute configuration of a stereocenter; a straight solid bond  and a straight dashed bond  indicate the relative configuration of a stereocenter; a wavy line  indicates a wedged solid bond  or a wedged dashed bond ; or a wavy line  indicates a straight solid bond  or a straight dashed bond .

Unless otherwise specified, the term "enriched in one isomer", "isomer enriched", "enriched in one enantiomer" or "enantiomeric enriched" means that the content of one isomer or enantiomer is less than 100%, and the content of the isomer or enantiomer is 60% or more, or 70% or more, or 80% or more, or 90% or more, or 95% or more, or 96% or more, or 97% or more, 98% or more, 99% or more, 99.5% or more, 99.6% or more, 99.7% or more, 99.8% or more, or 99.9% or more.

Unless otherwise specified, the term "isomer excess" or "enantiomeric excess" refers to the difference between the relative percentages of two isomers or two enantiomers. For example, if one isomer or enantiomer is present in an amount of 90% and the other isomer or enantiomer is present in an amount of 10%, the isomer or enantiomeric excess (ee value) is 80%.

Optically active (R)- and (S)-isomer, or D and L isomer can be prepared using chiral synthesis or chiral reagents or other conventional techniques. If one kind of enantiomer of certain compound disclosed herein is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereomer are generally isolated through chromatography which uses a chiral stationary phase and optionally combines with a chemical derivative method (for example, carbamate generated from amine).

The compounds disclosed herein may contain an unnatural proportion of atomic isotopes at one or more of the atoms that make up the compounds. For example, a compound may be labeled with a radioisotope such as tritium ($^3H$), iodine-125 ($^{125}I$) or C-14 ($^{14}C$). For another example, hydrogen can be replaced by heavy hydrogen to form a deuterated drug. The bond between deuterium and carbon is stronger than that between ordinary hydrogen and carbon. Compared with undeuterated drugs, deuterated drugs have advantages of reduced toxic side effects, increased drug stability, enhanced efficacy, and prolonged biological half-life of drugs. All changes in the isotopic composition of compounds disclosed herein, regardless of radioactivity, are included within the scope of the present disclosure.

The term "substituted" means one or more than one hydrogen atom (s) on a specific atom are substituted by a substituent, including deuterium and hydrogen variants, as long as the valence of the specific atom is normal and the substituted compound is stable. When the substituent is oxo (i.e., =O), it means two hydrogen atoms are substituted. Positions on an aromatic ring cannot be substituted by oxo. The term "optionally substituted" means an atom can be substituted by a substituent or not, unless otherwise specified, the species and number of the substituent may be arbitrary so long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as $-(CRR)_0-$, it means that the linking group is a single bond.

When the number of a substituent is 0, it means that the substituent does not exist. For example, $-A-(R)_0$ means that the structure is actually -A.

When a substituent is vacant, it means that the substituent does not exist. For example, when X in A-X is vacant, it means that the structure is actually A.

When one of the variables is a single bond, it means that the two groups linked by the single bond are connected directly. For example, when L in A-L-Z represents a single bond, the structure of A-L-Z is actually A-Z.

When the bond of a substituent can be cross-linked to two or more atoms on a ring, such a substituent can be bonded to any atom on the ring, for example, the structural unit

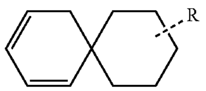 or 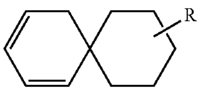

means that the substitution with substituent R can occur at any position on cyclohexyl or cyclohexadiene. When an enumerative substituent does not indicate through which atom it is linked to the substituted group, such substituent can be bonded through any of its atoms. For example, a pyridyl group as a substituent may be linked to the substituted group through any one of carbon atoms on the pyridine ring.

When an enumerative linking group does not indicate its linking direction, its linking direction is arbitrary. For example, when the linking group L in

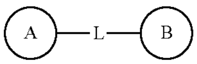

is -M-W—, the -M-W— can be linked to the ring A and the ring B in the same direction as the reading order from left to right to constitute

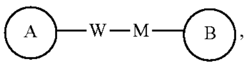, or can be linked to the ring A and the ring B in the reverse direction as the reading order from left to right to constitute

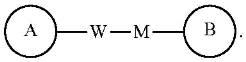.

A combination of the linking groups, substituents and/or variants thereof is allowed only when such combination can result in a stable compound.

Unless otherwise specified, when a group has one or more connectable sites, any one or more sites of the group can be connected to other groups through chemical bonds. Where the connection position of the chemical bond is variable, and there is H atom(s) at a connectable site(s), when the connectable site(s) having H atom(s) is connected to the chemical bond, the number of H atom(s) at this site will correspondingly decrease as the number of the connected chemical bond increases, and the group will become a group of corresponding valence. The chemical bond between the site and other groups can be represented by a straight solid bond , a straight dashed bond , or a wavy line . For example, the straight solid bond in $-OCH_3$ indicates that the group is connected to other groups through the oxygen atom in the group; the straight dashed bond in

indicates that the group is connected to other groups through two ends of the nitrogen atom in the group; the wavy line in

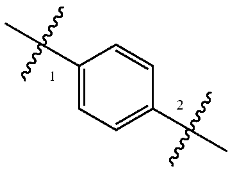 [SMILES: *c1ccc(*)cc1]

indicates that the group is connected to other groups through the 1- and 2-carbon atoms in the phenyl group;

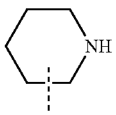

indicates that any connectable site on the piperidyl group can be connected to other groups through one chemical bond, including at least four connection ways

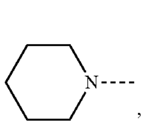, 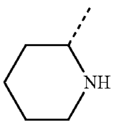, 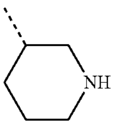 and

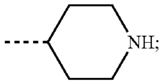

even if a H atom is drawn on —N—,

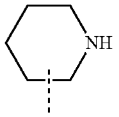

still includes the connection way of

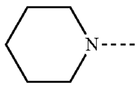

it's just that when one chemical bond is connected, the H at this site will be reduced by one, and the group will become the corresponding monovalent piperidyl group.

Unless otherwise specified, the number of atoms in a ring is generally defined as the number of ring members, e.g., "5-7 membered ring" refers to a "ring" having 5-7 ring atoms arranged.

Unless otherwise specified, "5-6 membered ring" means cycloalkyl, heterocycloalkyl, cycloalkenyl, heterocycloalkenyl, cycloalkynyl, heterocycloalkynyl, aryl, or heteroaryl consisting of 5 to 6 ring atoms. Said ring includes single ring, and also includes bicyclic ring systems such as spiro, fused and bridged rings. Unless otherwise specified, the ring optionally contains 1, 2 or 3 heteroatoms independently selected from O, S and N. The 5-6 membered ring includes 5-membered, 6-membered ring and the like. "5-6 membered ring" includes, for example, phenyl, pyridyl, piperidyl, and the like; on the other hand, the term "5-6 membered heterocycloalkyl" includes piperidyl and the like, but does not include phenyl. The term "ring" also includes a ring system containing at least one ring, wherein each "ring" independently meets the above definition.

Unless otherwise specified, "$C_{5-6}$ cycloalkyl" means a saturated cyclic hydrocarbon group consisting of 5 to 6 carbon atoms, which is a monocyclic ring system, that may be monovalent, divalent or polyvalent. Examples of $C_{5-6}$ cycloalkyl groups include, but are not limited to, cyclopentyl, cyclohexyl, and the like.

Unless otherwise specified, $C_{n-n+m}$ or $C_n$-$C_{n+m}$ includes any one of n to n+m carbons. For example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$. $C_{n-n+m}$ or $C_n$-$C_{n+m}$ also includes any range of n to n+m. For example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, $C_{9-12}$, and the like. Similarly, the n-membered to n+m-membered ring means that the number of atoms on the ring is n to n+m. For example, 3- to 12-membered ring includes 3-membered ring, 4-membered ring, 5-membered ring, 6-membered ring, 7-membered ring, 8-membered ring, 9-membered ring, 10-membered ring, 11-membered ring, and 12-membered ring. The n-membered to n+m-membered ring also means that the number of atoms on the ring includes any range from n to n+m. For example, 3- to 12-membered ring includes 3- to 6-membered ring, 3- to 9-membered ring, 5- to 6-membered ring, 5- to 7-membered ring, 6- to 7-membered ring, 6- to 8-membered ring, and 6- to 10-membered ring, and the like.

Unless otherwise specified, the term "5-6 membered heterocycloalkyl", by itself or in combination with another term, refers to a saturated cyclic group composed of 5 to 6 ring atoms respectively, in which 1, 2, 3 or 4 ring atoms are heteroatoms independently selected from O, S and N, and the rest are carbon atoms, wherein the nitrogen atom is optionally quaternized, and the nitrogen and sulfur heteroatoms can optionally be oxidized (i.e., NO and $S(O)_p$, p is 1 or 2). It includes monocyclic and bicyclic systems, wherein the bicyclic system includes spiro, fused, and bridged rings. In addition, in terms of the "5-6 membered heterocycloalkyl", the heteroatom can occupy the position through which the heterocycloalkyl is attached to the rest of the molecule. The 5-6 membered heterocycloalkyl includes 5-membered and 6-membered heterocycloalkyls. Examples of the 5-6 membered heterocycloalkyl include, but not limited to, pyrrolidinyl, pyrazolidinyl, imidazolidinyl, tetrahydrothiophenyl (including tetrahydrothiophen-2-yl and tetrahydrothiophen-3-yl etc.), tetrahydrofuranyl (including tetrahydrofuran-2-yl etc.), tetrahydropyranyl, piperidyl (including 1-piperidyl, 2-piperidyl and 3-piperidyl etc.), piperazinyl (including 1-piperazinyl and 2-piperazinyl etc.), morpholinyl (including 3-morpholinyl and 4-morpholinyl etc.), dioxanyl, dithianyl, isoxazolidinyl, isothiazolidinyl, 1,2-oxazinyl, 1,2-thiazinyl, hexahydropyridazinyl, homopiperazinyl or homopiperidyl.

Unless otherwise specified, the term "$C_{1-3}$ alkyl" is used to indicate a linear or branched saturated hydrocarbon group consisting of 1 to 3 carbon atoms. The $C_{1-3}$ alkyl group includes $C_{1-2}$ and $C_{2-3}$ alkyl groups and the like. It may be monovalent (e.g., methyl), divalent (e.g., methylene) or multivalent (e.g., methenyl). Examples of $C_{1-3}$ alkyl groups include, but are not limited to, methyl (Me), ethyl (Et), propyl (including n-propyl and isopropyl), and the like.

Unless otherwise specified, the term "$C_{1-3}$ alkoxy" means alkyl groups containing 1 to 3 carbon atoms and attached to the remainder of a molecule by an oxygen atom. The $C_{1-3}$ alkoxy group includes $C_{1-2}$, $C_{2-3}$, $C_3$, and $C_2$ alkoxy groups, and the like. Examples of $C_{1-3}$ alkoxy groups include, but are not limited to, methoxy, ethoxy, propoxy (including n-propoxy and isopropoxy), and the like.

The compound disclosed herein can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The alternative embodiment includes, but is not limited to the embodiment disclosed herein.

The structures of the compounds of the present disclosure can be confirmed by conventional methods well known to those skilled in the art. If the present disclosure relates to an absolute configuration of a compound, the absolute configuration can be confirmed by conventional techniques in the art, such as single crystal X-Ray diffraction (SXRD). In the single crystal X-Ray diffraction (SXRD), the diffraction intensity data of the cultivated single crystal is collected using a Bruker D8 venture diffractometer with a light source of CuKα radiation in a scanning mode of φ/ω scan; after collecting the relevant data, the crystal structure is further analyzed by the direct method (Shelxs97) to confirm the absolute configuration.

All the solvents used in the present disclosure are commercially available.

The present disclosure employs the following abbreviations: DMSO represents dimethyl sulfoxide; HCl represents hydrochloric acid; and ACN represents acetonitrile.

Compounds are named according to general naming principles in the art or by ChemDraw® software, and commercially available compounds are named with their vendor directory names.

DETAILED DESCRIPTION OF THE INVENTION

The present disclosure is described in detail below by means of examples. However, it is not intended that these examples have any disadvantageous limitations to the present disclosure. The present disclosure has been described in detail herein, and the embodiments are also disclosed herein. It will be apparent to those skilled in the art that various changes and modifications may be made to the embodiments disclosed herein without departing from the spirit and scope disclosed herein.

Example 1: Preparation of Compound 1

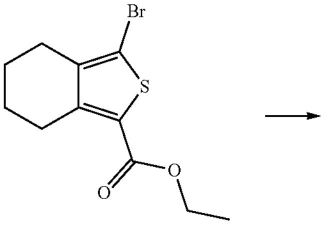

1-1

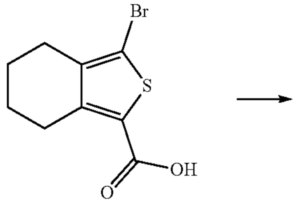

1-2

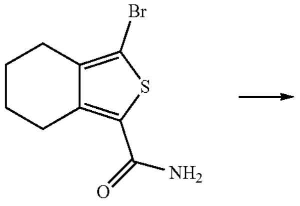

1-3

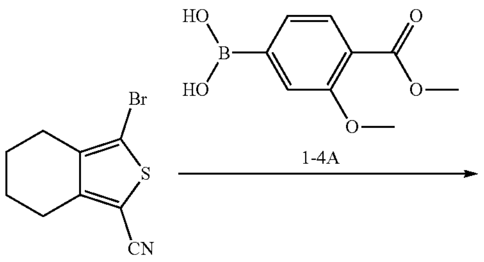

1-4A 1-4

-continued

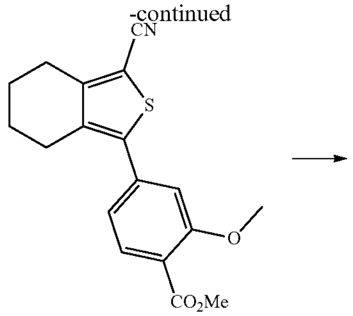

1-5

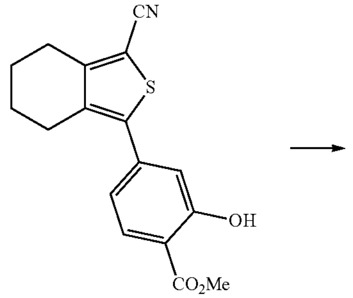

1-6

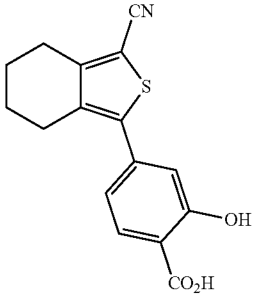

1

Step 1: Synthesis of Compound 1-2

Compound 1-1 (1.0 g, 3.46 mmol) was dissolved in a mixed solvent of methanol (5 mL) and water (5 mL), and then sodium hydroxide (276.62 mg, 6.92 mmol) was added. The resulting reaction solution was stirred at 55° C. for 4 hours. The methanol was removed by rotary-evaporated, and the residue was adjusted to pH 2-3 with 2M hydrochloric acid. A large amount of solid was precipitated. The solid was collected by filtration to give a crude product, which was added to ethyl acetate/petroleum ether (V/V=1:1, 3 mL) and the mixture was stirred at room temperature for 10 minutes. The solid was collected by filtration, and dried under vacuum at 45° C. for 30 minutes to give the compound 1-2. $^1$H NMR: (400 MHz, $CDCl_3$) δ: 3.06-3.00 (m, 2H), 2.59-2.52 (m, 2H), 1.81-1.68 (M, 4H); MS (ESI): m/z 260.9 $[M+H]^+$.

Step 2: Synthesis of Compound 1-3

Compound 1-2 (390 mg, 1.49 mmol) was dissolved in dichloromethane (2 mL), and then carbonyldiimidazole (290.60 mg, 1.79 mmol) was added. The resulting reaction solution was stirred at 25° C. for 1 hour. The reaction solution was then poured into aqueous ammonia (1.54 g, 7.47 mmol, 1.69 mL, 17% content), and then stirred vigorously for 20 minutes. The solvent was evaporated to give the crude product, and then purified by silica gel column chromatography (ethyl acetate/petroleum ether=0-35%) to give the compound 1-3. $^1$H NMR: (400 MHz, $CDCl_3$) δ: 5.56 (brs, 1H), 2.99-2.94 (m, 2H), 2.59-2.53 (m, 2H), 1.81-1.74 (m, 4H); MS (ESI): m/z 259.6 $[M+H]^+$.

Step 3: Synthesis of Compound 1-4

Compound 1-3 (271 mg, 1.04 mmol) was dissolved in N,N-dimethylformamide (1 mL), and the resulting solution was cooled to 0° C., and then cyanuric chloride (230.52 mg, 1.25 mmol) was added to afford the final reaction solution. The ice bath was removed, and the reaction solution was stirred at room temperature of 25° C. for 1 hour. The reaction solution was diluted with ethyl acetate (20 mL), and then washed with water (3 mL×3). The organic phase was dried with an appropriate amount of anhydrous sodium sulfate, then filtrated and the solvent was removed under reduced pressure to give the crude product. The crude product was purified by silica gel column chromatography (ethyl acetate/petroleum ether=0-3%) to give the compound 1-4.

Step 4: Synthesis of Compound 1-5

Compound 1-4 (82 mg, 338.65 μmol), boronic acid 1-4A (106.67 mg, 507.98 μmol) and potassium carbonate (93.61 mg, 677.31 μmol) were dissolved in a mixed solvent of dioxane (2 mL) and water (0.4 mL), and then 1,1'-bis (diphenylphosphino)ferrocene]palladium dichloride (Pd (dppf)$Cl_2$) (24.78 mg, 33.87 μmol) was added. After gas in the system was fully replaced by nitrogen, the reaction solution was placed in an oil bath at 110° C. and stirred for 18 hours. The solvent was evaporated to give the crude product, which was purified by silica gel column chromatography (ethyl acetate/petroleum ether=0-20%) to give compound 1-5. MS (ESI): m/z 327.9 $[M+H]^+$.

Step 5: Synthesis of Compound 1-6

Compound 1-5 (40 mg, 122.18 μmol) was dissolved in anhydrous dichloromethane (0.5 mL) and cooled to 0° C. with an ice bath, and then boron tribromide (61.22 mg, 244.35 μmol, 23.54 μL) was added under nitrogen. The obtained reaction solution was stirred at 25° C. for 2 hours. Water (0.5 mL) was added to quench the reaction in an ice-water bath, and then ethyl acetate (10 mL) was added and stirred to dissolution. The obtained solution was washed with water (2 mL×2), and the organic phase was evaporated to give the crude compound 1-6. The crude product was used directly in the next step.

Step 6: Synthesis of Compound 1

Compound 1-6 (37.83 mg, 120.71 μmol) was dissolved in tetrahydrofuran (1 mL) and water (1 mL), and then lithium hydroxide monohydrate (15.20 mg, 362.12 μmol) was added. The resulting reaction solution was stirred at 25° C. for 15 hours. The solvent was removed under reduced pressure, then the residue was adjusted to pH 2-3 with 1M hydrochloric acid. The crude product was purified by preparative HPLC (chromatographic column: Venusil ASB Phenyl 150*30 mm*5 μm; mobile phase: [Water (0.05% HCl)-ACN]; ACN %: 65%-95%, 9 min) to give Compound 1.

$^1$H NMR: (400 MHz, MeOD-$d_4$) δ: 7.96 (d, J=8.0 Hz, 1H), 7.13-7.05 (m, 2H), 2.90 (t, J=6.4 Hz, 2H), 2.83 (t, J=6.4 Hz, 2H), 1.93-1.77 (m, 4H). MS (ESI): m/z 299.9 $[M+H]^+$.

Example 2: Preparation of Compound 2

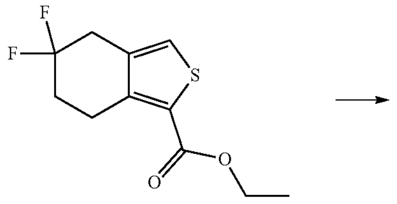

2-1

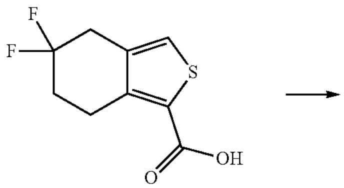

2-2

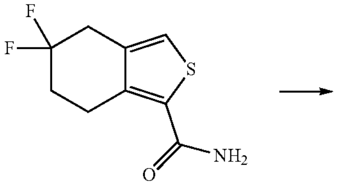

2-3

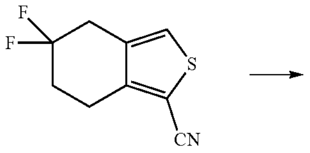

2-4

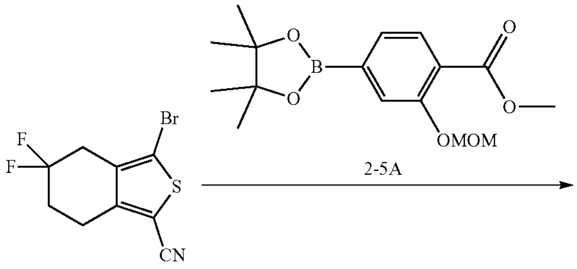

2-5

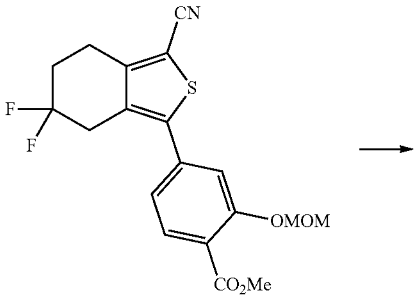

2-6

-continued

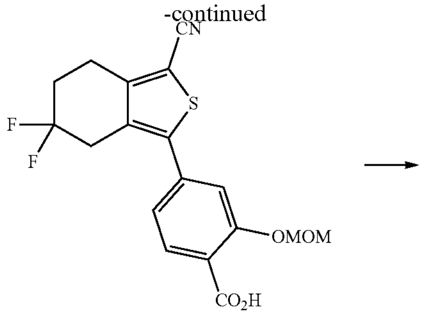

2-7

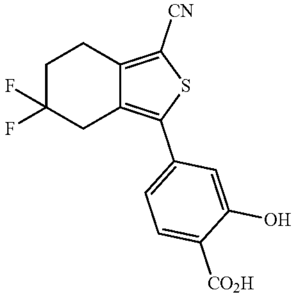

2

Step 1: Synthesis of Compound 2-2

Compound 2-1 (2.5 g, 10.15 mmol) was dissolved in methanol (10 mL), and water (10 mL) and sodium hydroxide (1.62 g, 40.61 mmol) were added. The resulting reaction solution was placed in an oil bath at 40° C. and stirred for 2 hours. The reaction solution was concentrated under reduced pressure to half volume, and water (5 mL) was added to the residue. 6M hydrochloric acid was used to adjust pH=2-3 under stirring, and a large amount of white solid was precipitated. The solid was collected by filtration and dried under vacuum at 50° C. for 3 hours to give the compound 2-2. $^1$H NMR (400 MHz, $CDCl_3$) δ: 7.28 (s, 1H), 3.30 (t, J=7.0 Hz, 2H), 3.22 (t, J=14.3 Hz, 2H), 2.25 (tt, J=6.8, 13.4 Hz, 2H).

Step 2: Synthesis of Compound 2-3

Compound 2-2 (500 mg, 2.29 mmol) was dissolved in dichloromethane (5 mL), and then carbonyldiimidazole (445.83 mg, 2.75 mmol) was added. The resulting reaction solution was stirred under nitrogen for 1 hour, and then poured into vigorously stirred ammonia water (2.87 g, 22.91 mmol, 3.15 mL, content 28%) in tetrahydrofuran (5 mL). The reaction solution was stirred for 30 minutes, concentrated under reduced pressure at 25° C., and the residue was extracted with ethyl acetate (20 mlx3). The organic phases were combined, and rotary-evaporated to give a crude product. The crude product was purified by silica gel column chromatography (ethyl acetate/petroleum ether=0-45%) to give the compound 2-3. $^1$H NMR (400 MHz, $CDCl_3$) δ: 7.10 (s, 1H), 5.58 (br s, 2H), 3.28 (t, J=6.9 Hz, 2H), 3.21 (t, J=14.4 Hz, 2H), 2.24 (tt, J=6.9, 13.4 Hz, 2H).

Step 3: Synthesis of Compound 2-4

Compound 2-3 (320 mg, 1.47 mmol) was dissolved in DMF (3 mL), and cooled to 0° C. Then cyanuric chloride (298.81 mg, 1.62 mmol) was added, and the reaction solution was stirred under nitrogen for 2 hours (a large amount of white solid was precipitated during this time). The reaction solution was diluted with ethyl acetate (50 mL), then washed with water (10 mL×3) and saturated brine (10 mL), dried with an appropriate amount of anhydrous sodium sulfate, filtrated and the solvent was removed under reduced pressure to give the crude compound 2-4, which was used directly in the next step. $^1$H NMR: (400 MHz, $CDCl_3$) δ: 7.25 (s, 1H), 3.21 (t, J=14.3 Hz, 2H), 3.09 (t, J=6.9 Hz, 2H), 2.28 (tt, J=6.8, 13.2 Hz, 2H).

Step 4: Synthesis of Compound 2-5

Compound 2-4 (290 mg, 1.46 mmol) was dissolved in acetic acid (2 mL), and then liquid bromine (348.94 mg, 2.18 mmol, 112.56 μL) was added. The reaction solution was stirred at 25° C. for 15 hours. The reaction solution was removed under reduced pressure, and ethyl acetate (30 mL) was added to the residue. The mixture was then adjusted to pH 7-8 with saturated sodium carbonate. The organic phase was separated, and the aqueous phase was extracted with ethyl acetate (30 mL). The combined organic phases were concentrated under reduced pressure to give a crude product. The crude product was purified by silica gel column chromatography (ethyl acetate/petroleum ether=0-5%) to give the compound 2-5. $^1$H NMR: (400 MHz, $CDCL_3$) δ: 3.10-2.99 m, 4H), 2.32-2.19 (m, 2H).

Step 5: Synthesis of Compound 2-6

Compound 2-5 (140 mg, 503.39 μmol), boronate 2-5A (178.39 mg, 553.73 μmol), and potassium carbonate (139.14 mg, 1.01 mmol) were dissolved in dioxane (3 mL) and water (0.6 mL), and then 1,1'-bis(diphenylphosphino)ferrocene] palladium dichloride ($Pd(dppf)Cl_2$) (36.83 mg, 50.34 μmol) was added. The reaction solution was heated to 105° C. under nitrogen and stirred for 15 hours. The reaction solution was removed under reduced pressure to give a crude product, which was purified by silica gel column chromatography (ethyl acetate/petroleum ether=0-25%) to give the compound 2-6. $^1$H NMR: (400 MHz, $CHCl_3$) δ: 7.87 (d, J=8.0 Hz, 1H), 7.28 (d, J=1.6 Hz, 1H), 7.10 (dd, J=1.6, 8.0 Hz, 1H), 5.0 (s, 2H), 3.3 (s, 3H), 3.55 (s, 3H), 3.23 (t, J=14.4 Hz, 2H), 3.13 (t, J=6.8 Hz, 2H), 2.39-2.24 (m, 2H).

Step 6: Synthesis of Compound 2-7

Compound 2-6 (105 mg, 266.90 μmol) was dissolved in tetrahydrofuran (2 mL), and then aqueous lithium hydroxide monohydrate (2 M, 533.80 μL) was added. The resulting reaction solution was stirred at 25° C. for 15 hours. Tetrahydrofuran was removed from the reaction solution under reduced pressure at 40° C., and the residue was adjusted to pH 2-3 with 2 M hydrochloric acid. A large amount of solid was precipitated. Ethyl acetate (50 mL) was added and the mixture was stirred. Ethyl acetate was separated out, and the mixture was rotary-evaporated to dryness to give the Compound 2-7. The crude product was used directly in the next step.

Step 7: Synthesis of Compound 2

Compound 2-7 (105 mg, 276.77 μmol) was dissolved in methanol (1 mL), and then hydrochloric acid (60.55 mg, 1.66 mmol, 59.36 μL) was added. The reaction solution became cloudy, and the reaction was stirred at 25° C. for 3 hours. The reaction solution was rotated-evaporated to dryness at 40° C., and the obtained residue was purified by preparative HPLC (chromatographic column: Venusil ASB Phenyl 150*30 mm*5 μm; mobile phase: [water (0.05% HCl)-ACN]; ACN %: 60%-90%, 9 min) to give the compound 2.

$^1$H NMR (400 MHz, MeOD-$d_4$) δ: 8.00 (d, J=8.0 Hz, 1H), 7.13-7.04 (m, 2H), 3.35-3.32 (m, 2H), 3.12 (t, J=7.2 Hz, 2H), 2.45-2.30 (m, 2H); MS (ESI) m/z: 334.02 $[M-H]^-$.

Example 3: Preparation of Compound 3

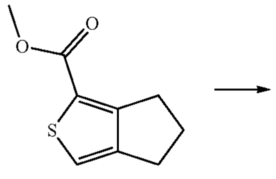

3-1

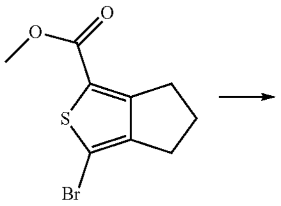

3-2

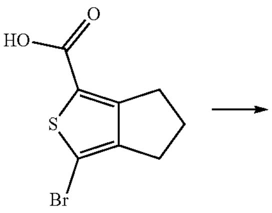

3-3

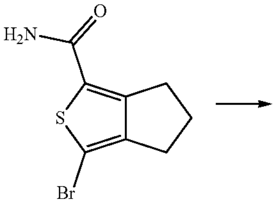

3-4

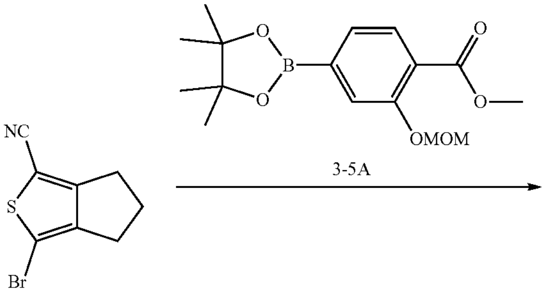

3-5A 3-5

-continued

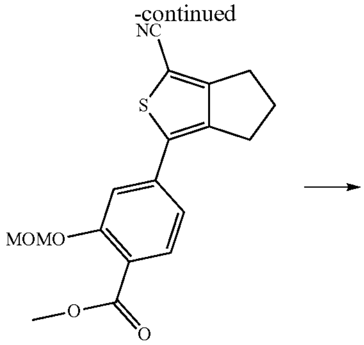

3-6

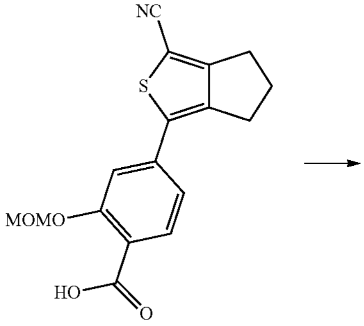

3-7

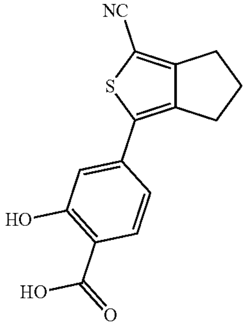

3

Step 1: Synthesis of Compound 3-2

Compound 3-1 (15.01 g, 82.36 mmol) was dissolved in N,N-dimethylformamide (80 mL), and then N-bromosuccinimide (23.46 g, 131.78 mmol) was added. The mixture was stirred at 25° C. for 12 h. The solvent was removed under reduced pressure, and the residue was dissolved in ethyl acetate (60 mL), washed with water (20 mL) and saturated brine (15 mL), and dried over anhydrous sodium sulfate, and filtrated, and the filtrate was evaporated under reduced pressure to remove solvent. Then the residue was purified by silica gel column chromatography (ethyl acetate/petroleum ether=0-15%) to give the compound 3-2. $^1$H NMR (400 MHz, $CDCl_3$) δ: 3.76 (s, 3H), 2.91 (t, J=7.2 Hz, 2H), 2.56-2.50 (m, 2H), 2.38-2.30 (m, 2H). MS (ESI): m/z 260.8 $[M+H]^+$.

Step 2: Synthesis of Compound 3-3

Compound 3-2 (1.98 g, 7.58 mmol) was dissolved in a mixed solution of methanol (10 mL) and water (10 mL), and then sodium hydroxide (606.54 mg, 15.16 mmol) was added. The reaction mixture was stirred at 50° C. for 1 hour.

After the reaction was completed, the solvent was removed under reduced pressure. Water (20 mL) was added to the residue, followed by washing with ethyl acetate (10 mL). The aqueous phase was adjusted to pH 4-5 with hydrochloric acid, and a large amount of gray-yellow solid was precipitated. After filtration, the filter cake was washed with water (10 mL), and then dried in vacuum to give the compound 3-3. $^1$H NMR (400 MHz, DMSO-d6) δ: 13.09 (brs, 1H), 2.90 (t, J=7.2 Hz, 2H), 2.58-2.53 (m, 2H), 2.39-2.33 (m, 2H); MS (ESI): m/z 246.8 $[M+H]^+$.

Step 3: Synthesis of Compound 3-4

Compound 3-3 (1.57 g, 6.36 mmol) was dissolved in dichloromethane (10 mL), and carbonyldiimidazole (1.24 g, 7.63 mmol) was added. The reaction solution was stirred at 25° C. for 1.5 hours under nitrogen, and then poured into a stirred solution of aqueous ammonia (3 M, 21.19 mL) in tetrahydrofuran. The mixture was stirred for another 0.5 h. The solvent was removed under reduced pressure, and then ethyl acetate (20 mL) was added. The resulting mixture was washed with water (10 mL) and then saturated brine (5 mL), and the organic layer was dried over anhydrous sodium sulfate, filtrated and the filtrate was evaporated to remove solvent under reduced pressure to give a crude product. The crude product was purified by silica gel column chromatography (ethyl acetate/petroleum ether=0-50%) to give the compound 3-4. $^1$H NMR (400 MHz, DMSO-$d_6$) δ 7.60-6.90 (m, 2H), 2.93 (t, J=8.0 Hz, 2H), 2.57-2.55 (m, 2H), 2.39-2.29 (m, 2H). MS (ESI): m/z 247.9 $[M+H]^+$.

Step 4: Synthesis of Compound 3-5

Compound 3-4 (550 mg, 2.23 mmol) was dissolved in N,N-dimethylformamide (6 mL), and cyanuric chloride (412.09 mg, 2.23 mmol) was added at 0° C. The reaction solution was warmed to 25° C., and stirred under nitrogen for 2 hours. A large amount of white solid was precipitated. The reaction solution was diluted with methyl tert-butyl ether (40 mL), then washed with water (10 mL) and saturated brine (5 mL). After the organic phase was dried over anhydrous sodium sulfate, filtrated and the solvent was removed under reduced pressure. The crude product was purified by silica gel column chromatography (ethyl acetate/petroleum ether=0-20%) to give the compound 3-5. $^1$H NMR (400 MHz, $CDCl_3$) δ: 2.82 (t, J=7.2 Hz, 2H), 2.59-2.52 (m, 2H), 2.44-2.35 (m, 2H).

Step 5: Synthesis of Compound 3-6

Compound 3-5 (150 mg, 657.58 μmol), boronate 3-5A (233.03 mg, 723.34 μmol) and 1,1'-bis(diphenylphosphino)ferrocene]palladium dichloride (Pd (dppf)$Cl_2$) (48.12 mg, 65.76 μmol) were put into the reaction flask, followed by potassium carbonate (181.76 mg, 1.32 mmol). Then, a mixture of water (0.6 mL) and dioxane (3 mL) was added, and the reaction solution was placed in an oil bath at 105° C. under nitrogen for 12 hours. The solvent was removed under reduced pressure to give a crude product, which was purified by silica gel column chromatography (ethyl acetate/petroleum ether=0-20%) to give the compound 3-6. $^1$H NMR (400 MHz, DMSO-$d_6$) δ:7.82 (d, J=8.0 Hz, 1H), 7.48 (s, 1H), 7.37-7.32 (m, 1H), 5.35 (s, 2H), 3.87 (s, 3H), 3.52 (s, 3H), 3.02 (t, J=8.0 Hz, 2H), 2.89 (t, J=8.0 Hz, 2H), 2.61-2.51 (m, 2H).

Step 6: Synthesis of Compound 3-7

Compound 3-6 (168 mg, 489.23 μmol) was dissolved in tetrahydrofuran (5 mL), and then lithium hydroxide (2 M, 1.47 mL) was added. The reaction was stirred at 23° C. for 2 hours. The pH was adjusted to 4-5 with 2M hydrochloric acid, and then tetrahydrofuran was removed under reduced pressure. Ethyl acetate (15 mL) was added to the residue, and the mixture was washed with water (5 mL) and saturated brine (5 mL). The organic phase was dried with an appropriate amount of anhydrous sodium sulfate, filtrated and the solvent was removed under reduced pressure to give the crude compound 3-7, which was used directly in the next step. MS (ESI): m/z 329.9 $[M+H]^+$.

Step 7: Synthesis of Compound 3

Compound 3-7 (160 mg, 485.78 μmol) was dissolved in methanol (2 mL), and hydrochloric acid (49.20 mg, 485.78 μmol, 48.23 μL, 36% pure) was added. After the reaction mixture was stirred at 23° C. for 3 hours, the solvent was removed under reduced pressure to give a crude product, which was purified by preparative HPLC (chromatographic column: Venusil ASB Phenyl 150*30 mm*5 μm; mobile phase: [water (0.05% HCl)-ACN]; ACN %: 55%-85%, 9 min) to give compound 3. $^1$H NMR (400 MHz, MeOD-$d_4$) δ: 7.97-7.92 (m, 1H), 7.45-7.21 (m, 2H), 3.01 (t, J=7.2 Hz, 2H), 2.89 (t, J=7.2 Hz, 2H), 2.65-2.51 (m, 2H); MS (ESI): m/z 286.0 $[M+H]^+$.

Example 4: Preparation of Compound 4

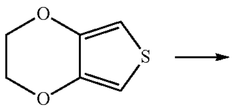

4-1

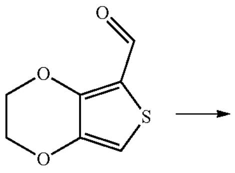

4-2

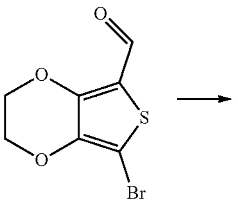

4-3

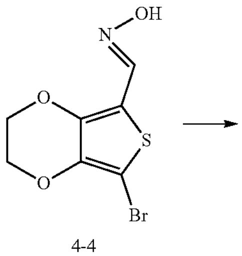

4-4

-continued

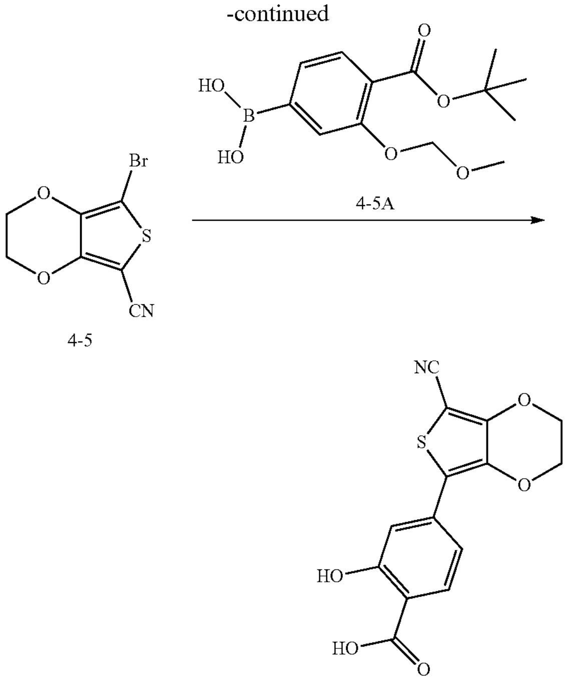

4-5A 4-5

4

Step 1: Synthesis of Compound 4-2

Compound 4-1 (1 g, 7.03 mmol) was dissolved in tetrahydrofuran (20 mL), and n-butyllithium (2.5 M, 3.10 mL) was added dropwise at −78° C. under nitrogen. After the mixture was stirred at this temperature for 30 minutes, N,N-dimethylformamide (950.00 mg, 13.00 mmol, 1.00 mL) was added dropwise. Then the mixture was heated to 23° C. for 1 h. Hydrochloric acid was added to adjust the pH to 2-3, and a solid was precipitated in the solution. The precipitated solid was filtered, and the filter cake was washed with 5 mL of water, and then dried under vacuum to give the compound 4-2. $^1$H NMR (400 MHz, $CDCl_3$) δ: 9.94 (s, 1H) 6.82 (s, 1H) 4.37-4.41 (m, 2H) 4.28-4.31 (m, 2H).

Step 2: Synthesis of Compound 4-3

Compound 4-2 (200 mg, 1.18 mmol) was dissolved in DMF (3 mL), and N-bromosuccinimide (250.99 mg, 1.41 mmol) was added, then the resulting reaction solution was stirred at 23° C. for 48 hours. After the reaction was completed, the solvent was removed under reduced pressure, and the residue was diluted with ethyl acetate (20 mL), and washed with water (3 mL*2) and saturated brine (2 mL), and the organic phase was dried over anhydrous sodium sulfate. The solvent was removed under reduced pressure again to give a crude product, which was purified by column chromatography (ethyl acetate/petroleum ether=0-20%) to give the compound 4-3. $^1$H NMR (400 MHz, $CDCl_3$) δ: 9.85 (s, 1H), 4.45-4.30 (m, 4H); LCMS m/z=246.9 $[M+H]^+$.

Step 3: Synthesis of Compound 4-4

Compound 4-3 (215 mg, 863.17 μmol) was dissolved in ethanol (4 mL), and aqueous hydroxylamine solution (50%, 114.04 mg, 1.73 mmol) was added, then the reaction solution was refluxed at 90° C. for 2 hours. After the reaction was completed, the solvent was directly removed under reduced pressure. Acetonitrile (4 mL) was added, and the solvent was removed again to give the compound 4-4. MS (ESI): m/z 263.9 $[M+H]^+$ Step 4: Synthesis of Compound 4-5

Compound 4-4 (130 mg, 492.24 μmol) was dissolved in acetonitrile (5 mL), and thionyl chloride (234.25 mg, 1.97 mmol, 142.84 μL) was added under nitrogen. The mixture was heated to reflux at 90° C. for 4 hours. The solvent was removed under reduced pressure and the residue was purified by column chromatography (ethyl acetate/petroleum ether=0-30%) to give the compound 4-5. $^1$H NMR (400 MHz, $CDCl_3$) δ: 4.32-4.41 (m, 4H); MS (ESI): m/z 247.0 $[M+H]^+$.

Step 5: Synthesis of Compound 4

Compound 4-5 (110 mg, 447.01 μmol), 4-5A (138.71 mg, 491.71 μmol) and potassium carbonate (123.56 mg, 894.01 μmol) were dissolved in dioxane (2 mL)/water (0.4 mL), and then Pd(dppf)$Cl_2$ (32.71 mg, 44.70 μmol) was added under nitrogen. The resulting reaction solution was heated to 105° C. for 15 hours. The reaction solution was concentrated, and trifluoroacetic acid (2 mL) was added. The reaction solution was stirred at room temperature for 1 hour and concentrated, and the residue was dissolved in dimethyl sulfoxide (3 mL) and purified by preparative HPLC (column: AgelaASB 150*25 mm*5 μm; mobile phase: [water (0.05% HCl)-ACN]; Acetonitrile %: 46%-76%, 9 min) to give compound 4. $^1$H NMR (400 MHz, DMSO_$d_6$) δ: 7.86 (d, J=8.4 Hz, 1H), 7.34-7.24 (m, 2H), 4.49 (d, J=6.4 Hz, 4H). MS (ESI): m/z 302.0 $[M-H]^-$.

Example 5: Preparation of Compound 5

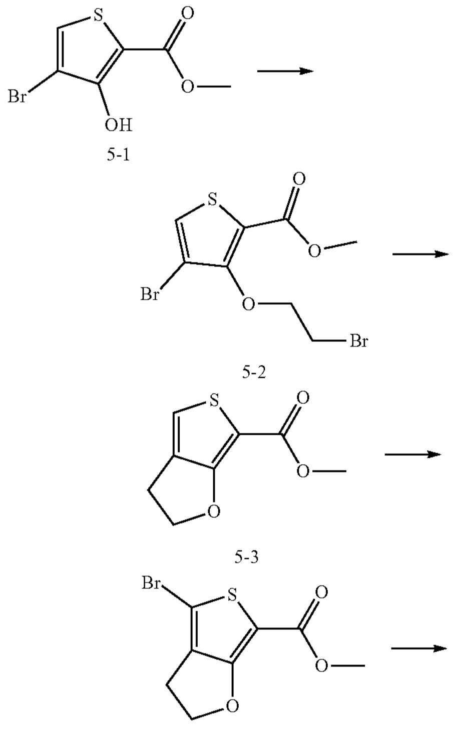

5-1

5-2

5-3

5-4

-continued

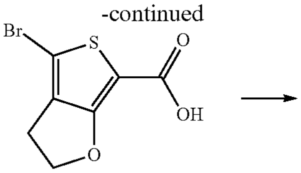

5-5

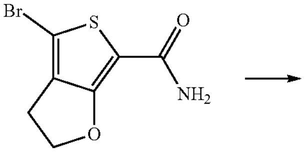

5-6

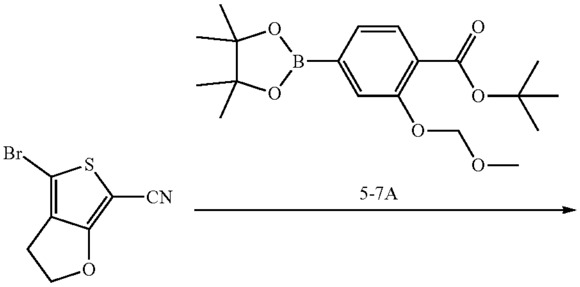

5-7A 5-7

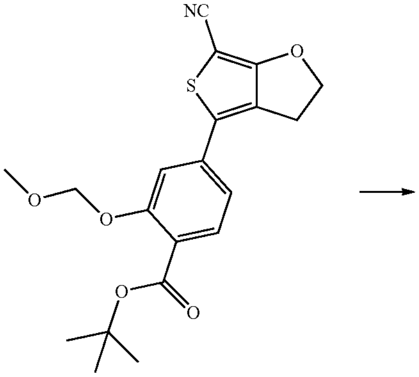

5-8

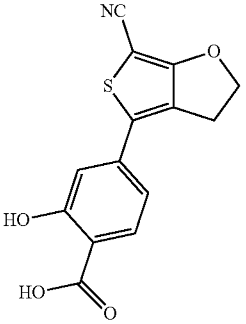

5

Step 1: Synthesis of Compound 5-2

Compound 5-1 (5 g, 21.09 mmol), 1,2-dibromoethane (31.70 g, 168.73 mmol, 12.73 mL) and potassium carbonate (11.66 g, 84.36 mmol) were dissolved in N,N-dimethylformamide (50 mL), and the mixture was heated to 85° C. for 4 hours. The reaction solution was concentrated, and 100 mL of ethyl acetate was added. The mixture was stirred for 10 minutes and filtrated, and the filtrate was concentrated under reduced pressure to give a crude product. The crude product was purified by column chromatography (ethyl acetate/petroleum ether=0-2%) to give the compound 5-2. $^1$H NMR (400 MHz, $CDCl_3$) δ: 7.41 (s, 1H) 4.49 (t, J=6.8 Hz, 2H), 3.89 (s, 3H), 3.70 (t, J=6.8 Hz, 2H).

Step 2: Synthesis of Compound 5-3

Compound 5-2 (6.5 g, 18.89 mmol) was dissolved in tetrahydrofuran (60 mL), and the solution was stirred and cooled to −78° C. Then n-butyllithium (2.5 M, 7.56 mL) was added dropwise. Then the reaction mixture was stirred at this temperature for 2 hours. The reaction was quenched by saturated ammonium chloride solution (20 mL) and water (30 mL), and the organic phase was separated. The aqueous phase was extracted with ethyl acetate (50 mL), and the combined organic phases were concentrated, the crude product was purified by column chromatography (ethyl acetate/petroleum ether=0-35%) to give the compound 5-3. $^1$H NMR (400 MHz, $CDCl_3$) δ: 6.95 (s, 1H), 5.10 (t, J=8.4 Hz, 2H), 3.86 (s, 3H), 3.04 (t, J=8.4 Hz, 2H).

Step 3: Synthesis of Compound 5-4

Compound 5-3 (620 mg, 3.37 mmol) was dissolved in N,N-dimethylformamide (5 mL), and then N-bromosuccinimide (898.56 mg, 5.05 mmol) was added. The resulting reaction solution was stirred at 25° C. for 24 hours. The solvent was removed under reduced pressure, and the residue was dissolved in ethyl acetate (50 mL). The solution was washed with saturated sodium bisulfite (10 mL) and saturated brine (10 mL). The organic phase was concentrated, the crude product was purified by column chromatography (ethyl acetate/petroleum ether=0-25%) to give the compound 5-4. MS (ESI): m/z 262.9 $[M+H]^+$.

Step 4: Synthesis of Compound 5-5

Compound 5-4 (318 mg, 1.21 mmol) was dissolved in methanol (2 mL), and then sodium hydroxide solution (2 M, 1.21 mL) was added. The reaction solution was stirred at 45° C. for 2 hours. The reaction solution was concentrated, and water (2 mL) was added to the residue. The pH was adjusted to about 2-3 with 6M hydrochloric acid, and a large amount of precipitation was precipitated. After stirring for 10 minutes, it was collected by filtration, and the filter cake was dried in vacuum at 45° C. for 2 hours to give the compound 5-5. MS (ESI): m/z 248.9 $[M+H]^+$.

Step 5: Synthesis of Compound 5-6

Compound 5-5 (250 mg, 1.00 mmol) was dissolved in dichloromethane (3 mL), and then carbonyldiimidazole (244.12 mg, 1.51 mmol) was added. The resulting reaction solution was stirred under nitrogen for 1 hour. Then the reaction solution was poured into ammonia water (1.30 g, 10.04 mmol, 1.43 mL, 27% concentration) in tetrahydrofuran solution (5 mL), and the reaction was stirred for 30 minutes. The reaction solution was concentrated, and the residue was dissolved in ethyl acetate (50 mL). The solution was washed with water (10 mL) and saturated brine (10 mL). The organic phase was dried with an appropriate amount of anhydrous sodium sulfate, and filtrated, and the filtrate was concentrated under reduced pressure to give the crude compound 5-6, which was used directly in the next step. MS (ESI): m/z 249.9 $[M+H]^+$.

Step 6: Synthesis of Compound 5-7

Compound 5-6 (230 mg, 927.06 μmol) was dissolved in N,N-dimethylformamide (3 mL), and then cyanuric chloride (256.44 mg, 1.39 mmol) was added. The resulting reaction solution was stirred at 25° C. for 2 hours. The reaction solution was diluted with ethyl acetate (80 mL), and then washed with water (20 mL) and saturated brine (20 mL). The organic phase was dried with an appropriate amount of anhydrous sodium sulfate, and filtrated, and the filtrate was concentrated under reduced pressure to give a crude product. The crude product was purified by column chromatography (ethyl acetate/petroleum ether=0-15%) to give the compound 5-7. MS (ESI): m/z 252.2 $[M+Na]^+$.

Step 7: Synthesis of Compound 5-8

Compound 5-7 (130 mg, 565.02 μmol), 5-7A (308.70 mg, 847.53 μmol) and potassium carbonate (195.22 mg, 1.41 mmol) were dissolved in dioxane (1.5 mL) and water (0.3 mL), and then $Pd(dppf)Cl_2$ (82.69 mg, 113.00 μmol) was added under nitrogen. The resulting reaction solution was heated to 110° C. for 15 hours. The reaction solution was concentrated, and the residue was purified by column chromatography (ethyl acetate/petroleum ether=0-25%) to give the compound 5-8. MS (ESI): m/z 388.1 $[M+H]^+$.

Step 8: Synthesis of Compound 5

Compound 5-8 (140 mg, 361.34 μmol) was dissolved in dichloromethane (0.5 mL), and then trifluoroacetic acid (412.01 mg, 3.61 mmol, 267.54 μL) was added. The resulting reaction solution was stirred at 25° C. for 2 hours. The reaction solution was concentrated and the residue was dissolved in N,N-dimethylformamide (5 mL). The solution was purified by preparation HPLC (chromatographic column: Venusil ASB Phenyl 150*30 mm*5 μm; mobile phase: [water (0.05% HCl)-ACN]; acetonitrile %: 45%-75%, 9 min) to give the compound 5. $^1H$ NMR (400 MHz, $CD_3OD$) δ: 7.96 (d, J=8.8 Hz, 1H), 7.20-7.05 (m, 2H), 5.20 (t, J=8.0 Hz, 2H), 3.39 (t, J=8.0 Hz, 2H). MS (ESI): m/z 286.0 $[M-1]^-$.

Biological Test Data:

Assay Example 1: Xanthine Oxidase Inhibitory Activity Test 1.1 Purpose of the Assay Compounds were evaluated for the level of inhibiting xanthine oxidase activity.

1.2 Reagent

The main reagents used in this study included xanthine (Sigma, Cat. No. X4002-1G, Lot: SLBB5664V) and xanthine oxidase (Sigma, Cat. No. X4376-5UN, Lot: SLBQ1518V).

1.3 Instrument

The main instrument used in this study is a multi-function microplate reader.

1.4 Method of the Assay 1) 50 μL of Dulbecco's Phosphate Buffered Saline (DPBS) was added to background control wells of compounds and positive control wells (HPE: 100% inhibitory activity).
2) 2 U/mL of xanthine oxidase was diluted with DPBS to 0.04 U/mL, and 50 μL xanthine oxidase was added to the compound wells and negative control wells (ZPE: 0% inhibitory activity).
3) The compounds were serially 3-fold diluted with DMSO for 8 points, then the compound was diluted with DPBS, and 50 μL of the mix was added to each well in triple wells. 50 μL of DPBS was added to each well of positive control wells (HPE: 100% inhibitory activity) and negative control wells (ZPE: 0% inhibitory activity).
4) 200 mM xanthine was diluted to 300 μM with DPBS. 100 μL of xanthine was added to each well. The mixture was pre-treated at room temperature for 30 minutes. The final concentration of xanthine oxidase in each well was 0.01 U/mL, and the final concentration of DMSO in each well was 0.5%. Positive control wells (HPE: 100% inhibitory activity) contained xanthine but no xanthine oxidase, and negative control wells (ZPE: 0% inhibitory activity) contained xanthine and xanthine oxidase. Compound background control wells contained various concentrations of the compound and xanthine but without xanthine oxidase.
5) Detecting the absorbance value at 290 nm with a spectrophotometer.
6) Data analysis: calculating the inhibition of xanthine oxidase in each well according to the following equation:

$$\text{Inhibition}\,\% = \left(1 - \frac{OD_{test\ sample} - OD_{compound\ control}}{OD_{ZPE} - OD_{HPE}}\right) * 100\%$$

*$OD_{test\ sample}$ is the optical density value of the compound activity test well, containing the compound, xanthine and xanthine oxidase;

$OD_{compound\ control}$ is the background optical density value of the compound to be tested at different concentrations, containing the compound and xanthine, without xanthine oxidase;

$OD_{ZPE}$: the mean value of optical density of the negative control wells, containing 0.5% DMSO, xanthine and xanthine oxidase;

$OD_{HPE}$ is the mean value of optical density of the positive control wells, containing 0.5% DMSO and xanthine, without xanthine oxidase.

7) GraphPad Prism software was used to perform log (agonist) vs. response—Variable slope nonlinear fitting analysis on the inhibition data (inhibition %) of the compound to give the $IC_{50}$ value of the compound. The fitting formula:

$$Y=\text{Bottom}+(\text{Top}-\text{Bottom})/(1+10\hat{}((\text{Log IC}_{50}-X)*\text{HillSlope}))$$

1.5 Assay Results

TABLE 1

Results of xanthine oxidase inhibitory activity test of the compounds

| Compound Number | XO $IC_{50}$ (nM) |
|---|---|
| Compound 1 | 25.0 |
| Compound 2 | 20.7 |

TABLE 1-continued

| Results of xanthine oxidase inhibitory activity test of the compounds | |
|---|---|
| Compound Number | XO $IC_{50}$ (nM) |
| Compound 3 | 25.9 |
| Compound 4 | 22.8 |
| Compound 5 | 24.0 |

The assay results show that the compounds have good xanthine oxidase inhibitory activity.

Assay Example 2: Inhibitory Activity Test of the Compounds on Uric Acid Uptake 1. Purpose of the Assay In this study, human Uratl gene stably transfected cell lines were used to evaluate the inhibitory activity of the test compounds on uric acid uptake.

2. Materials of the Assay 2.1 Cell Lines

The human Uratl gene stably transfected cell line was constructed by WuXi AppTec. Human Uratl gene stably transfected cell line (Uratl-MDCK) is MDCK cells transfected with human Uratl gene and obtained by G418 screening. Uratl-MDCK cells were cultured in MEM medium containing 10% fetal bovine serum (FBS), 100 U/ml penicillin, 100 μg/ml streptomycin, 2 mM L-glutamine and 1% non-essential amino acids, and 250 μg/ml G418.

2.2 Reagent

The main reagent used in this study included $^{14}C$-uric acid (ARC, Cat. No. ARC-0513, Lot No. 200122).

2.3 Instrument

The main instrument used in this study was a liquid scintillation analyzer (Perkin Elmer, Tri-Carb 4910TR).

3. Method of the Assay 3.1 Cell Plating 3.1.1 The Uratl-MDCK cells cultured in the T150 cell culture flask were digested with 0.25% trypsin, then adjusted to a suspension with 200,000 cells/ml with fresh culture medium.

3.1.2 Cells were seeded into a 48-well cell culture plate at 0.5 ml per well at a final cell density of 100,000 cells/well.

3.1.3 The cell culture plate was incubated in a 37° C., 5% $CO_2$ incubator overnight.

3.2 Treatment with the Compounds and Detection 3.2.1 A serially 5-fold dilution of the compounds in DMSO was made for 4 points, and the diluted concentration was 200 times the final assay concentration. Compounds were then diluted 10-fold in HBSS buffer.

3.2.2 10 mM concentrated stock solution of $^{14}C$-uric acid was diluted to 1 mM with HBSS buffer.

3.2.3 After the cell culture plate was incubated overnight, the cell culture medium was removed from the plate, and the cells were washed three times with HBSS buffer followed by adding 90 μl of HBSS buffer to each well.

3.2.4 5 μl of diluted compound was added to each well, and the cells were incubated in a 37° C., 5% $CO_2$ incubator for 20 minutes. The final concentration of DMSO in each well was 0.5%. The test compound (10 μM) was used as a 100% inhibition control, and 0.5% DMSO was used as a 0% inhibition control.

3.2.5 5 μl per well diluted $^{14}C$-uric acid was added to the cell plate, and the final concentration of uric acid in each well was 50 μM. The cells were incubated in a 37° C., 5% $CO_2$ incubator for 15 minutes. Cells were then washed 3 times with pre-chilled HBSS buffer. 3.2.6 150 μl 0.1M NaOH was added to each well to lyse cells for 10 minutes.

3.2.7 The cell lysate was collected into liquid scintillation detection vial, and 2 ml of scintillation fluid was added to each vial for testing.

3.2.8 The $^{14}C$ content of sample in each tube was detected with a liquid scintillation analyzer.

3.2.9 Data analysis:

$$\text{Inhibition } \% = (HC - CPD)/(HC - LC) \times 100\% *$$

*CPD is the radioactive signal value of the compound well;

HC is the mean value of the radioactive signal from the 0% inhibition control wells;

LC is the mean value of radioactive signal from the 100% inhibition control wells.

3.2.10 Using GraphPad Prism software, the nonlinear regression log(inhibitor) vs. response—Variable slope method was adopted to fit the dose-response curve according to the following formula, and the $IC_{50}$ and $IC_{90}$ values of the compounds were obtained.

$$Y=\text{Bottom}+(\text{Top}-\text{Bottom})/(1+10\hat{}((\text{Log } IC_{50}-X)*\text{HillSlope}))$$

4. Assay Results

TABLE 2

| Inhibitory activity of the compounds on uric acid uptake | |
|---|---|
| Compound Number | $IC_{50}$ (μM) |
| Compound 2 | 2.24 |
| Compound 3 | 4.05 |
| Compound 4 | 36.88 |
| Compound 5 | 45.45 |

Conclusion: Assay results show that the compounds of the present disclosure have a good inhibitory activity on uric acid uptake

Assay Example 3: Hepatocytes Metabolic Stability (HMS) Study

1. Purpose of the Assay

To test the metabolic stability of the test sample in human and rat hepatocytes.

2. Materials of the Assay 2.1 Test compound (10 mM), control substance: 7-Ethoxycoumarin (30 mM), 7-Hydroxycoumarin (control substance, 30 mM)

2.2 Cell

| Hepatocyte | cell viability | Supplier Cat No. |
|---|---|---|
| Rat hepatocytes | 85% | BioreclamationIVTM00005 |
| Human hepatocytes | 84% | Bioreclamation IVTX008001 |

2.3 Buffer System:

Thawing medium: Williams' medium E containing 5% fetal bovine serum, 30% Percoll solution and other auxiliary materials Incubation medium: Williams medium E (without phenol red) containing 2 mM L-glutamine and 25 mM hydroxyethylpiperazine ethane sulfonic acid.

Stop solution: 200 ng/mL of tosylbutyramide and labetalol in acetonitrile as internal standards.

Dilution solution: Ultrapure water.

3. Method of the Assay

1) The exact amount of positive control compound was dissolved in dimethyl sulfoxide (DMSO) to give a 30 mM solution 2) 10 mM test compound and 30 mM positive control compound were diluted to 1 mM and 3 mM with DMSO in 96-well plates.

3) 1 mM test compound and 3 mM positive control compound was diluted into 100 μM and 300 μM quantification solutions with acetonitrile.

4) The cryopreserved cells were thawed, dissociated and suspended in culture medium, and then diluted to $0.5\times10^6$ cells/mL with pre-warmed culture medium.

5) 198 μL of pre-warmed cell suspension was added to a 96-well plate.

6) 100 μL of stop solution (acetonitrile containing 200 ng/mL tosylbutyramide and 200 ng/mL labetalol as internal standard) was transferred in a set of pre-labeled 96-well plates.

7) 2 μL of 100 μM test compound or 300 μM positive control quantitation solution was added in duplicate to each well of the 96-well plate.

8) The TO samples were mixed to achieve uniform suspension over about 1 min, and then 20 μL of each sample was immediately transferred into wells containing 100 μL of ice-cold stop solution followed by mixing.

9) All plates were incubated at 37° C. in 5% $CO_2$ in a 95% humidified incubator, with constant shaking at approximately 600 rpm for reaction.

10) At 15, 30, 60 and 90 min, samples were mixed, and then 20 μL of each sample was transferred to wells containing 100 μL of ice-cold stop solution at each time point and mixed.

11) Medium control (MC) sample plates (labeled as TO-MC and T90-MC) were prepared at TO and T90 by adding the same components to each well except for the cell suspension. Final concentration table was obtained.

12) At each respective time point, the reaction was stopped by removing the plate from the incubator and mixing with 100 μL of ice-cold stop solution.

13) Immediately vortexing the plate on a plate shaker at 500 rpm for 10 minutes. Then, all sample plates were centrifuged at 3220×g at 4° C. for 20 min.

14) After centrifugation, 35 μL/well of the supernatant from the sample plate was transferred to another set of pre-labeled 96-well plates containing 70 μL of ultrapure water according to the plate diagram.

15) The assay plates were sealed and stored at 4° C. until LC-MS-MS analysis.

The residual ratio of the test compound and the control compound was obtained by the following formula:

$$\text{Residual ratio}(\%) = \frac{\text{Peak area ratio of compound to internal satndard at any time point}}{\text{Peak area ratio of compound to internal standard at 0 minutes}} \times 100\%$$

The elimination rate constant k of the test compound and the control compound in hepatocytes was calculated by plotting the logarithm of the residual ratio vs time, and the half-life ($T_{1/2}$) and in vitro intrinsic clearance rate ($CL_{int}$) were obtained by using the elimination rate k. The formula as follows:

$$T_{1/2}=0.693/k$$

$$CL_{int(hep)}=k/\text{Cells per ml (million cells/mL)}$$

$$CL_{int(liver)}=CL_{int(hep)}\times\text{Liver weight to weight ratio}\times\text{number of hepatocytes per gram of liver}$$

The parameters of the species in the formula were as follows:

| Species | Liver weight to weight ratio (g/kg) | Hepatic blood flow ($Q_h$) (mL/min/kg) | Number of hepatocytes (cells per gram of liver) |
|---|---|---|---|
| Mouse | 88 | 90.0 | $135 \times 10^6$ |
| Rat | 40 | 55.2 | $117 \times 10^6$ |
| Dog | 32 | 30.9 | $215 \times 10^6$ |
| Monkey | 30 | 43.6 | $120 \times 10^6$ |
| Human | 20 | 20.7 | $139 \times 10^6$ |

4. Assay Results

The results are shown in Table 3.

TABLE 3

Intrinsic clearance rates of the compounds in human and rat liver

| Compound Number | Intrinsic hepatic clearance (mL/min/Kg) Human | Rat |
|---|---|---|
| Compound 2 | 31.8 | 188.4 |
| Compound 3 | 48.2 | 1097.9 |

Conclusion: Compound 2 and compound 3 are both at moderate clearance in human hepatocytes and at high clearance in rat hepatocytes.

Assay Example 4. Membrane Permeability MDR1 Test

1. Purpose of the Assay:

MDR1-MDCK II cells are Madin-Darby canine kidney cells transfected with human MDR1 gene, which can stably express high P-gp. The aim of this study was to test the bidirectional permeability of compounds across the MDR1-MDCK II cell model and to assess whether they are transported by efflux.

2. Cell Culture:

MDR1-MDCK II cells (obtained from Piet Borst, Netherlands Cancer Institute) were seeded at a density of $2.5\times10^5$ cells/mL onto polyethylene membrane (PET) in a 96-well insert for 4-7 days until forming fusion cell monolayer.

3. Method of the Assay

Test compounds were diluted in transport buffer (HBSS, 10 mM Hepes with DMSO, pH 7.4) to a concentration of 2 μM (DMSO<1%) and applied on the apical or basolateral side of the cell monolayer. The compound to be tested was tested in duplicate in the direction of from A to B or from B to A, digoxin was tested at 10 μM in the direction of from A to B or from B to A, while nadolol and metoprolol were tested at 2 μM from A to B. Plates were incubated in a $CO_2$ incubator at 37±1° C. in a saturated humidity of 5% $CO_2$ for 2.5 hours without shaking. In addition, the efflux ratio of each compound was determined, and for the test and reference compounds quantitation was conducted. Analysis was carried out by LC/MS/MS according to the peak area ratio of analyte/IS. After the transport assay, the Lucifer Yellow exclusion assay was used to determine integrity of the cell monolayer. The buffer was removed from the apical and basolateral compartments, then 75 μL of 100 μM luciferin yellow was added to the transport buffer, and 250 μL of the transport buffer was added to the apical and basolateral compartments, respectively. The plate was incubated at 37° C., 5% $CO_2$ and saturated humidity for 30 minutes without shaking. After 30 minutes of incubation, 20 μL of luciferin yellow sample was withdrawn from the apical, followed by the addition of 60 μL of transport buffer. An 80 μL luciferin yellow sample was then collected basolaterally. Relative fluorescence units (RFU) of luciferin yellow were measured at 425/528 nm (excitation/emission) with an Envision microplate reader.

4. Data Calculation

The apparent permeability coefficient ($P_{app}$, cm/s), efflux rate and recovery rate were calculated using the following formulae.

The apparent permeability coefficient ($P_{app}$, cm/s) was calculated using the following formula:

$$P_{app} = (dC_r/d_t) \times V_r/(A \times C_0)$$

$dC_r/d_t$ is the cumulative concentration of the compound at the receiver end over unit time (μM/s); $V_r$ is the volume of the receiver end solution (0.075 mL and 0.250 mL for the apical and basal ends, respectively); Ais the relative surface area (0.0804 $cm^2$) of the cell monolayer; $C_0$ is the initial concentration (nM) of the test substance at the administration end or the peak area ratio of the reference substance.

The efflux ratio was calculated using the following formula:

$$\text{Efflux ratio} = P_{app}(BA)/P_{app}(AB)$$

The recovery rate was calculated using the following formula:

$$\%\ \text{Recovery} = 100 \times [(V_r \times C_r) + (V_d \times C_d)]/(V_d \times C_0)$$

$C_0$ is the initial concentration (nM) of the test substance at the administration end or the peak area ratio of the reference substance; Va is the volume of the administration end (0.075 mL for the apical side and 0.250 mL for the basal side); $C_d$ and $C_r$ are the final concentration (nM) of the test substance at the administration end and the receiver end or the peak area ratio of the reference substance.

The percentage of Lucifer Yellow in the basolateral pores was calculated using the following formula:

$$\%\ \text{Lucifer Yellow} = \frac{V_{Basolatera\ l} \times RFU_{Basolatera\ l}}{V_{Apical} \times RFU_{Apical} + V_{Basolatera\ l} \times RFU_{Basolatera\ l}} \times 100$$

wherein RFUApical and RFUBasolateral are the relative fluorescence unit values of Lucifer Yellow in the apical and basolateral pores, respectively; VApical and VBasolateral are the volumes of the apical and basolateral pores (0.075 mL and 0.25 mL), respectively. % Lucifer Yellow should be less than 2.

5. Assay Results

The results are shown in Table 4.

TABLE 4

Data of membrane permeability of the compounds to MDR1 cell

| Compound Number | $P_{app}$ (AB) ($10^{-6}$ cm/s) | $P_{app}$ (BA) ($10^{-6}$ cm/s) | Efflux ratio |
|---|---|---|---|
| Compound 2 | 26.42 | 6.63 | 0.25 |
| Compound 3 | 38.63 | 10.99 | 0.28 |

Conclusion: Compound 2 and compound 3 both have high permeability.

Assay Example 5. Cytochrome P450 Isozyme Inhibitory Activity Test

1. Purpose of the Assay

The inhibitory activities of test compounds against different subtypes of human cytochrome P450 isoenzymes were determined.

2. Method of the Assay

Preparing test compounds, standard inhibitor (100×final concentration) and mixed substrate working solutions; Microsomes (purchased from Corning Inc) frozen in −80° C. freezer was taken out and thawed. 20 μL of the test compound and standard inhibitor solution were added to the corresponding wells, and at the same time 20 μL of the corresponding solvent was added to the no inhibitor control wells (NIC) and blank control wells (Blank); then 20 μL of mixed substrate solution was added to the corresponding wells, except for Blank wells (adding 20 μL of Phosphate Buffer (PB) to Blank wells); the human liver microsome solution was prepared (marking the date after use and putting back in the refrigerator immediately), then 158 μL of human liver microsome solution was immediately added to all wells; the above sample plate was pre-incubated in a 37° C. water bath, and then coenzyme factor (NADPH) solution was prepared; 10 minutes later, 20 μL of NADPH solution was added to all wells. After the sample plate was shaken well, it was incubated in a 37° C. water bath for 10 minutes; at the corresponding time point, 400 μL of cold acetonitrile solution (internal standard: 200 ng/mL tolbutamide and labetalol) was added to stop the reaction; After the sample plate was mixed well, it was centrifuged at 4000 rpm for 20 minutes to precipitate proteins; 200 μL of supernatant was taken out and added to 100 μL of water, the mix was shaked well, and then subjected to LC/MS/MS for detection.

3. Assay Results

The results are shown in Table 5.

TABLE 5

| $IC_{50}$ values of compounds for P450 isoenzyme inhibition | | | | | |
|---|---|---|---|---|---|
| Compound | Cytochrome P450 isoenzyme $IC_{50}$ (μM) | | | | |
| Number | CYP1A2 | CYP2C9 | CYP2C19 | CYP2D6 | CYP3A4-M |
| Compound 2 | >50 | 18.1 | >50 | >50 | >50 |
| Compound 3 | >50 | 14.8 | >50 | >50 | >50 |

Conclusion: The tested compounds have very low inhibitory activity on CYP1A2, CYP2C19, CYP2D6 and CYP3A4-M, and have moderate inhibitory activity on CYP2C9.

Assay Example 6: Pharmacokinetics in SD Rats

1. Purpose of the Assay:

Pharmacokinetics of test compounds in SD rats

2. Materials of the Assay:

Sprague Dawley Rat (male, 180-350 g, 6-10 weeks old, Charles River Laboratories, Beijing)

3. Method of the Assay:

Compound 2 was mixed with 5% DMSO/10% Solutol/85% water, and the mixture was stirred and vortexed to prepare a clear solution at 0.6 mg/mL for the administration of the injection group, and was filtered by a microporous membrane for use. Compound 2 was mixed with 5% DMSO/10% Solutol/85% water, and the mixture was stirred and vortexed to prepare a clear solution at 1 mg/mL for oral administration. Six male SD rats were divided into 2 groups. Animals in group 1 were administered intravenously in a single dose of 3 mg/kg, the vehicle was 5% DMSO/10% Solutol/85% water, and the administration volume was 5 mL/kg. Animals in the second group were administered with the test compound 2 by oral gavage in a single dose of 10 mg/kg, the oral vehicle was 5% DMSO/10% Solutol/85% water, and the oral volume was 10 mL/kg. Whole blood was collected at 0 (the gavage group only), 0.083 (intravenous only), 0.25, 0.5, 1, 2, 4, 8 and 24 hours after administration. Whole blood was centrifuged at 3200 g at 4° C. for 10 min to obtain plasma. The concentrations of Compound 2 and uric acid (the oral gavage group only) in plasma were determined by LC/MS/MS method, and the pharmacokinetic parameters, such as peak concentration, Time to peak, clearance rate, half-life, area under the curve, bioavailability, etc were calculated by Phoenix WinNonlin software.

Assay results are as follows in Table 6:

TABLE 6

| Pharmacokinetic data of compound 2 in rats | | | | | |
|---|---|---|---|---|---|
| 2.89 mpk Intravenous injection | | | | | |
| | $C_0$ (μM) | $T_{1/2}$ (hr) | $Vd_{ss}$ (L/kg) | Cl (mL/min/kg) | $AUC_{0\text{-}inf}$ (μM · hr) |
| Compound 2 | 96.6 | 3.74 | 0.32 | 3.59 | 41.8 |
| 8.58 mpk Oral | | | | | |
| | $C_{max}$ (μM) | $T_{max}$ (hr) | $T_{1/2}$ (hr) | $AUC_{0\text{-}inf}$ (μM · hr) | Bioavailability (%) |
| Compound 2 | 27.5 | 0.5 | 2.47 | 86.6 | 62.1 |

Conclusion: Compound 2 has good pharmacokinetic properties and high oral bioavailability. wherein, $C_0$ is the initial concentration, $T_{1/2}$ is the elimination half-life, $Vd_{ss}$ is the steady-state apparent volume of distribution, Cl is the total clearance, and $AUC_{0\text{-}last}$ is the area under the plasma concentration-time curve from time 0 to the last quantifiable time point, $AUC_{0\text{-}inf}$ is the area under the plasma concentration-time curve from time 0 to extrapolated infinity, $C_{max}$ is the peak concentration, and $T_{max}$ is the time to peak.

What is claimed is:

1. A compound represented by formula (I) or a pharmaceutically acceptable salt thereof, (I)

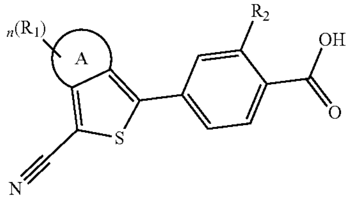

wherein, $R_2$ is OH; and the structural unit

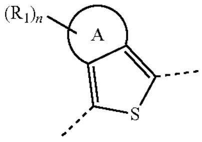

is selected from the group consisting of

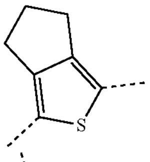
,
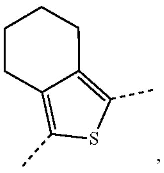
,
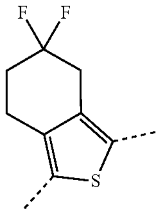
,
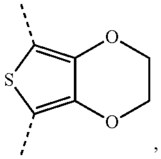
, and
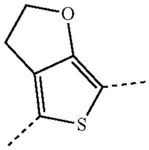
.

2. A compound represented by the following formula or a pharmaceutically acceptable salt thereof,

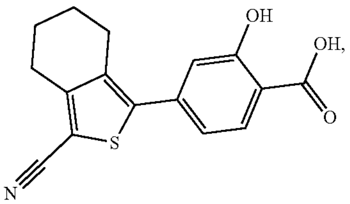

-continued

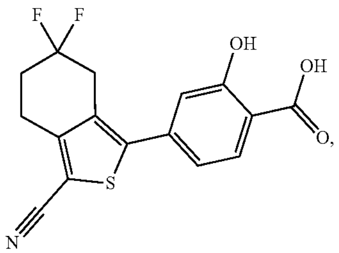

or

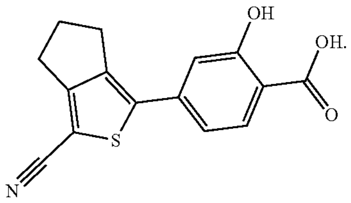

3. A method of treating a disease mediated by a xanthine oxidase in a subject, the method comprising administering to the subject the compound or the pharmaceutically acceptable salt thereof according to claim 1, wherein the disease is gouty arthritis or hyperuricemia.

4. A method of treating a disease mediated by a xanthine oxidase in a subject, the method comprising administering to the subject the compound or the pharmaceutically acceptable salt thereof according to claim 2, wherein the disease is gouty arthritis or hyperuricemia.

5. The compound of claim 1, or a pharmaceutically acceptable salt thereof, wherein the compound is:

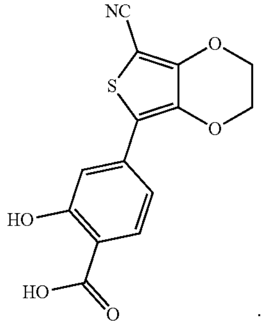 [SMILES: N#Cc1sc(-c2ccc(C(=O)O)c(O)c2)c2c1OCCO2]

6. The compound of claim 1, or a pharmaceutically acceptable salt thereof, wherein the compound is:

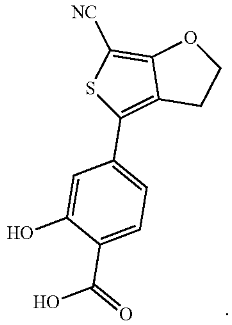 [SMILES: N#Cc1sc(-c2ccc(C(=O)O)c(O)c2)c2c1OCC2]

* * * * *